United States Patent [19]

Kupchan et al.

[11] 3,950,344
[45] Apr. 13, 1976

[54] NON-PHENOL OXIDATIVE COUPLING

[75] Inventors: Solomon Morris Kupchan, Charlottesville, Va.; Andris J. Liepa, Blakehurst, Australia

[73] Assignee: The University of Virginia, Charlottesville, Va.

[22] Filed: Sept. 13, 1973

[21] Appl. No.: 396,811

[52] U.S. Cl. 260/289 A; 260/239 BB; 260/239 BD; 260/239 D; 260/243 R; 260/244 R; 260/247.5 DP; 260/250 A; 260/251 Q; 260/283 SY; 260/288 R; 260/310 D; 260/326.16; 260/326.5 B
[51] Int. Cl.$^2$............ C07D 215/12; C07D 217/20; C07D 221/26
[58] Field of Search..... 260/289 R, 283 SY, 326.16, 260/289 A, 289 D

[56] References Cited
FOREIGN PATENTS OR APPLICATIONS
44-28113   11/1969   Japan.............................. 260/289 R

OTHER PUBLICATIONS

Kametani et al., "J. Chem. Soc.," (C), pp. 3315–3318 (1971).

Primary Examiner—R. Gallagher
Assistant Examiner—D. B. Springer
Attorney, Agent, or Firm—Oblon, Fisher, Spivak, McClelland & Maier

[57] ABSTRACT

Oxidative coupling of non-phenolic compounds is attained by subjecting said non-phenolic compound to oxidizing conditions in contact with an oxidant selected from the group of $VOF_3$, $MoOCl_4$, $Pb_3O_4$, $Tl(CF_3COO)_3$, $CrO_3$, $MnO_2$, $Co(OH)_3$, $Ce(SO_4)_2$, and $Ce(NH_4)_2(NO_3)_6$.

5 Claims, No Drawings

NON-PHENOL OXIDATIVE COUPLING

RIGHTS OF GOVERNMENT

The invention described herein was made in the course of work under a grant or award from the Department of Health, Education, and Welfare and therefore may be manufactured and used by or for the Government for governmental purposes without the payment of any royalties thereon or therefor.

BACKGROUND OF THE INVENTION

1. Field of the Invention:

This invention relates to a method of forming intermolecular and intramolecular carbon-carbon bonds in non-phenolic substrates.

2. Description of the Prior Art:

It is known that carbon-carbon bond formation can be induced in phenolic compounds by oxidation reactions. This bond formation mechanism has been used for various biosynthesis procedures and for synthesis procedures for the formation of complex alkaloids and other polycyclic compounds (see Taylor et al, "Oxidative Coupling of Phenols"; Marcel Dekher, NY-NY1967; and Kametani et al, Synthesis, 657 (1972)). Intramolecular coupling of monophenolic compounds is disclosed in Schwartz et al, J. Amer. Chem. Soc., 95, 612 (1973) and Kupchan et al, ibid, 95, 4062 (1973).

Heretofore, however, although electro-oxidative coupling of non-phenolic compounds has been reported, prior art attempts to effect such a coupling reaction by non-electrolytic, chemical means, have been unsuccessful (see Miller et al, ibid, 95, 2651 (1973)).

The chemical coupling of non-phenolic compounds, however, could open new synthesis routes for the formation of various biologically active compounds, and in particular biologically active complex alkaloids and polycyclic compounds, which heretofore have been synthesizable, if at all, with great difficulty.

A need exists, therefore, for a technique of effecting an oxidative coupling reaction whereby intermolecular coupling and intramolecular coupling of non-phenolic compounds can be effected.

SUMMARY OF THE INVENTION

Accordingly, it is one object of this invention to form oxidatively induced intermolecular or intramolecular coupling in non-phenolic compounds.

This and other objects of this invention can be attained by intermolecular oxidative coupling of non-phenolic compounds of the formula

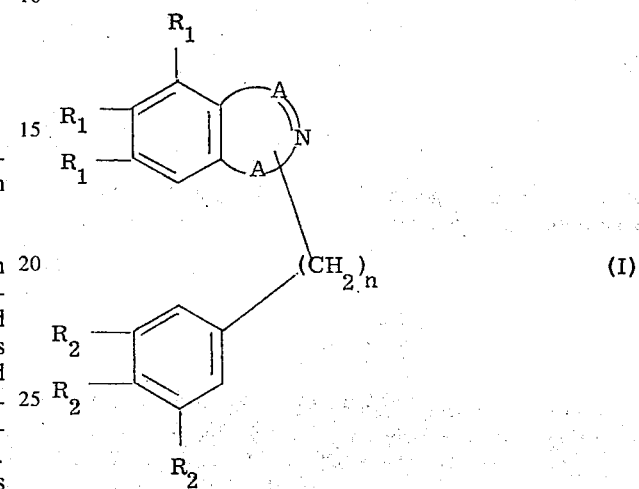

(I)

wherein $n$ is a integer of from $1-5$, each $R_1$ and $R_2$ may be lower alkyl having $1-7$ carbon atoms, lower alkoxy having $1-7$ carbon atoms or hydrogen, with the proviso that at least one $R_1$ and at least one $R_2$ are lower alkoxy, and wherein —A-N=A— represents an unsaturated heterocyclic nitrogen ring, with an oxidizing agent selected from the group consisting of $VOF_3$, $MoOCl_4$, $Pb_3O_4$, $Tl(CF_3COO)_3$, $CrO_3$, $MnO_2$, $Co(OH)_3$, $Ce(SO4)_2$, and $Ce(NH_4)_2(NO_3)_6$, to form a compound of the formula

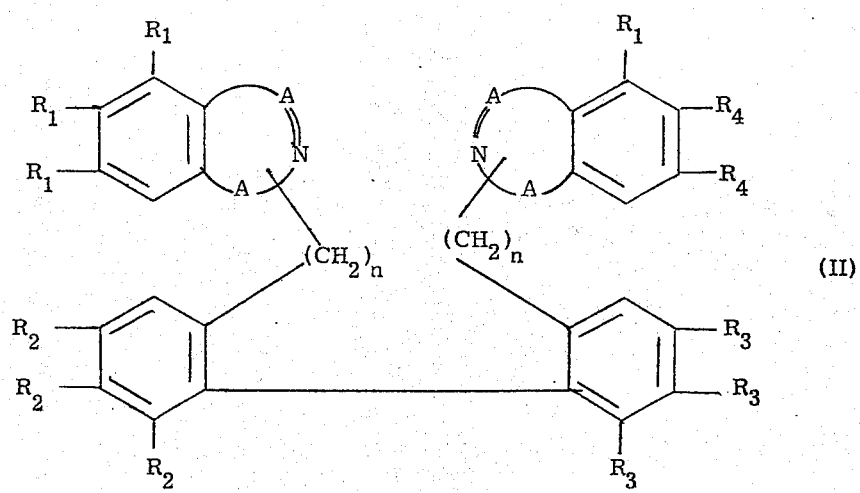

(II)

wherein $R_3$ and $R_4$ are the same as $R_2$ and $R_1$ respectively with the proviso that at least one of each of $R_1$, $R_2$, $R_3$ and $R_4$ are lower alkoxy.

Intramolecular coupling of non-phenolic compounds can be attained by oxidatively cyclizing a non-phenolic nitrogen heterocyclic of the formula

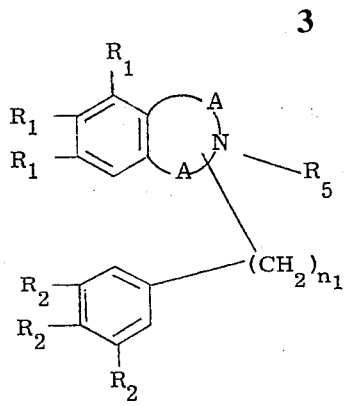 (III)

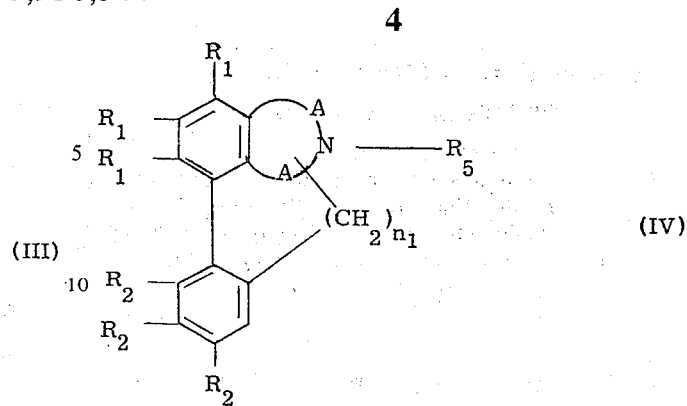 (IV)

wherein $n_1$ is a integer of from 1 – 3, $R_1$ and $R_2$ have been defind as above and $$-A-\overset{|}{N}-A-$$

represents a saturated heterocyclic ring having a $R_5$ substituted nitrogen, wherein $R_5$ is defined as a lower acyl group of the form RCO wherein R is a lower alkyl group having 1 – 7 carbon atoms, or hydrogen, or a lower alkyl group, of 1 – 7 carbon atoms, to form a cyclized compound of the formula This invention therefore provides a non-electrolytic, chemical, oxidative coupling of non-phenolic compounds.

DETAILED DESCRIPTION OF THE PREFERRED EMBODIMENTS

According to this invention the compound (I) or (III) is reacted in the presence of an oxidizing agent to either intermolecularly couple to form a dimer, (II) or to intramolecularly cycle, as shown in (IV).

The unsaturated heterocyclic ring in formula (I) may be any of the following:

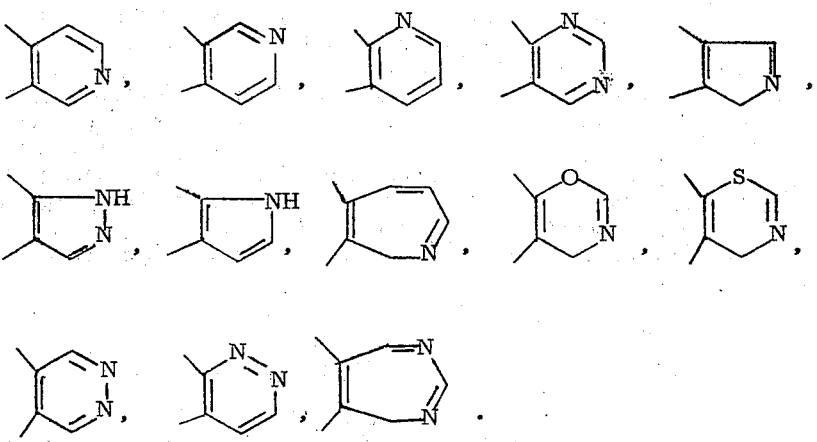

The saturated heterocyclic ring in formula (III) may be any of the following structures:

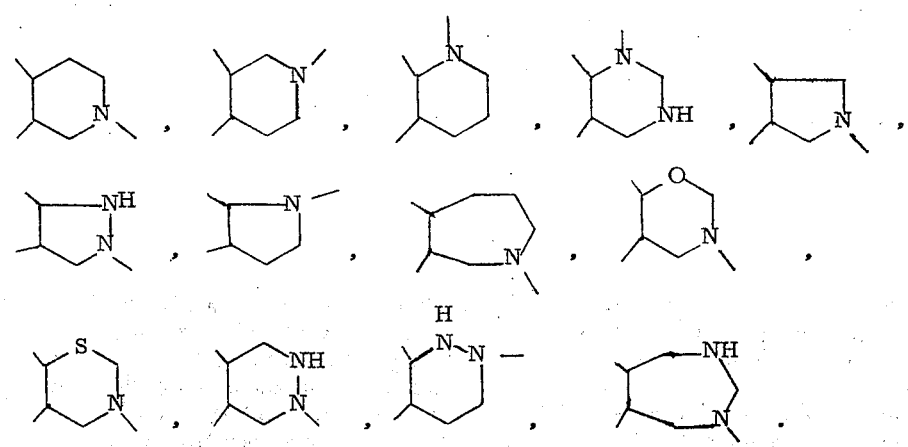

For instance, the unsaturated heterocyclic compound I may have the formula:
For instance, the saturated heterocyclic compound III may have the structure:
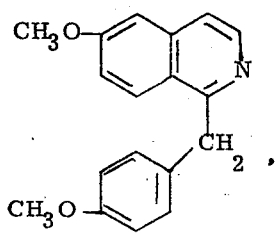 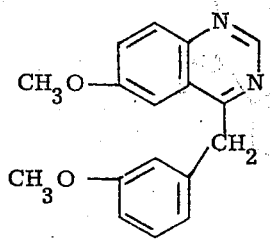 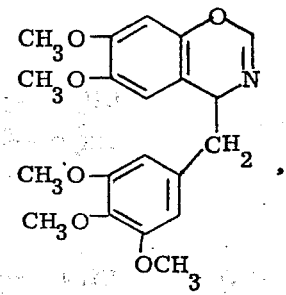
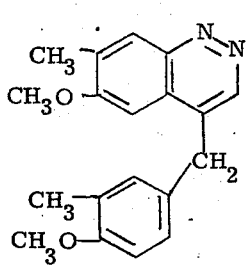 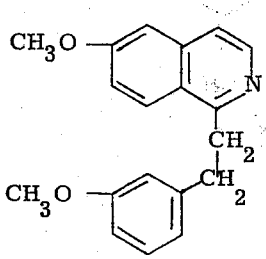 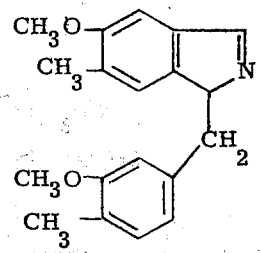
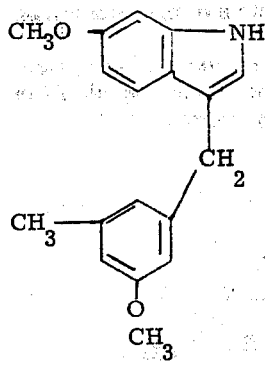 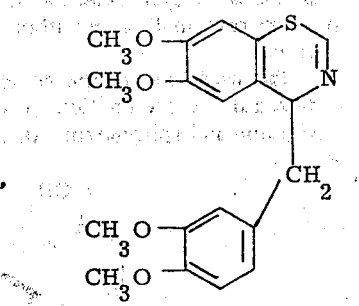
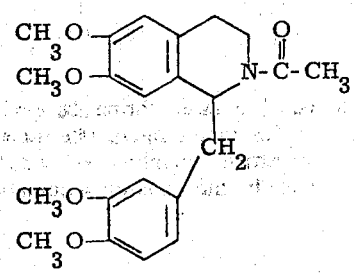
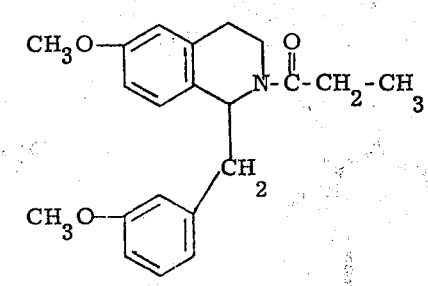 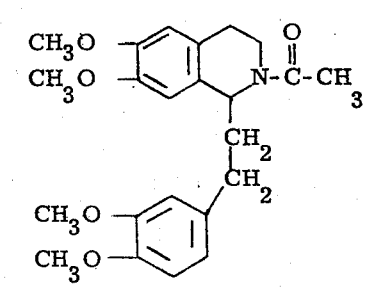

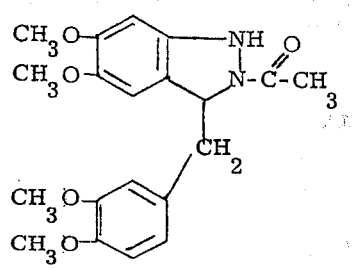
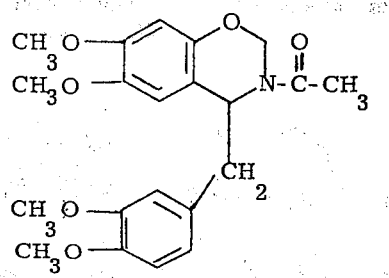

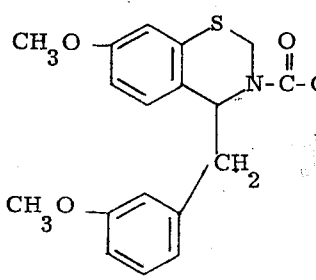
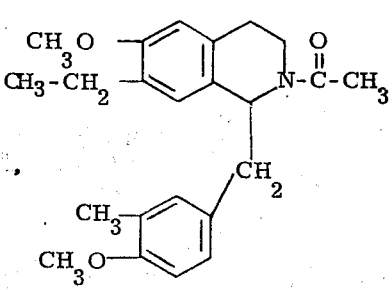

In effecting either intra- or intermolecular oxidative coupling, the reactions will proceed at relatively low temperatures of from −45° to 60°C, preferably from −30° to 30°C, with best results occurring from −30° to 0°C; by mixing the reactant (I) or (III) with a strong oxidizing agent of the type: VOF$_3$, MoOCl$_4$, Pb$_3$O$_4$, Tl(CF$_3$COO)$_3$ or Ce(SO$_4$)$_2$, Ce(NH$_4$)$_2$(NO$_3$)$_6$, Co(OH)$_3$, MnO$_2$ or CrO$_3$.

The ratio of oxidant to reactant may range from a molar ratio of 1 : 1 to 20 : 1.

The reaction may be effected in the presence of an acidic medium such as an aqueous medium containing sulfuric acid, trifluoroacetic acid, methylene chloride, acetonitrile, carbon tetrachloride, ethyl acetate, tetrahydrofuran, acetic acid or trifluoroacetic acid and trichloromethane, or mixtures thereof.

The reaction may be conducted at normal pressure, but can also be conducted under conditions of slight vacuum or above atmospheric pressure. The reaction period, of course, will vary depending upon the particular reactants and oxidant, but usually will range from 1 minute to 24 hours.

The nature of the R$_5$ group is critical in determining the course of intramolecular coupling. Thus, when R$_5$ is hydrogen or a lower alkyl group, the positive charge on the protonated basic nitrogen atom directs the coupling toward the non-heterocyclic rings. The acylation of the heterocyclic nitrogen by the presence of the R$_5$ acyl group neutralizes the effect of the basic nitrogen atom and causes cyclization or intramolecular coupling to occur principally to a carbon atom of the heterocyclic ring.

The usefulness of the novel reactions of this invention can be exemplified by the efficient synthesis of the unusual spirodienone of the formula

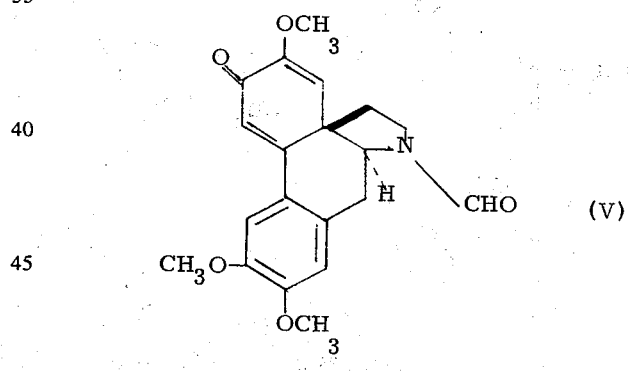

which is an erythrina alkaloid precursor.

This compound can be formed by the intramolecular oxidative coupling of (±)N-formylnor-laudanosine (VI) by the reaction schematic as follows:

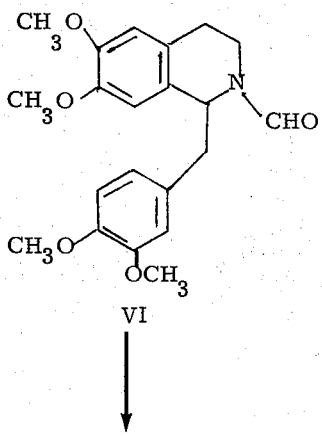
VI

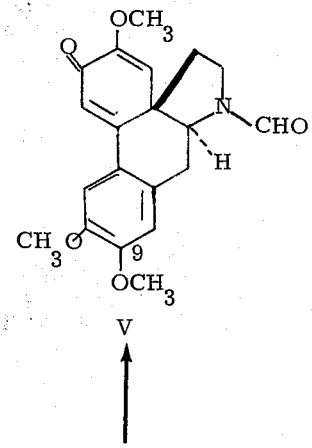
V

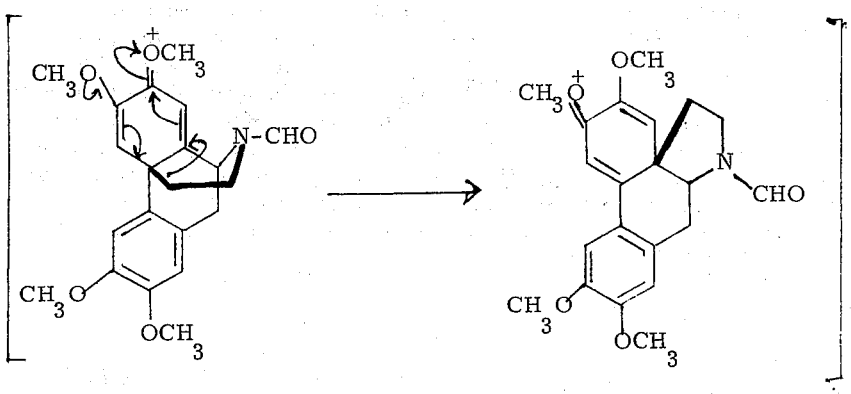

This precursor can be synthesized into the known useful hypotensive alkaloid pharmaceutical by the schematic

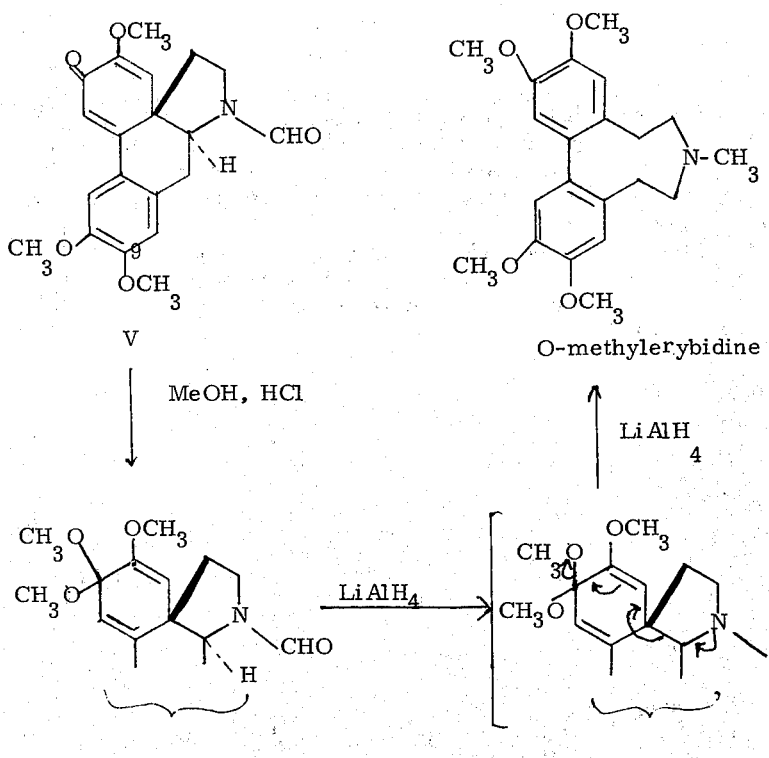

Protostephanine is a naturally occurring dibenzazonine derivative with a structure closely resembling O-methylerybidine. Analogs of protostephanine have been reported to have central depressant and hypotensive action, see A. Brossi et al, U.S. Pat. No. 3,457,295.

In general dibenzazonine derivative of the formula:

such as O-methylerybidine, may be formed by treating a ±N-formyl, 1-benzyl-1,2,3,4-tetrahydro-isoquinoline of the formula

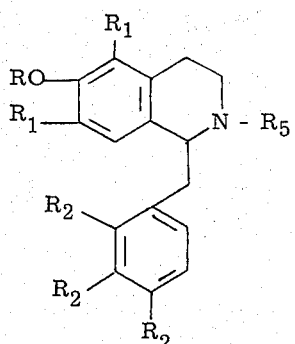

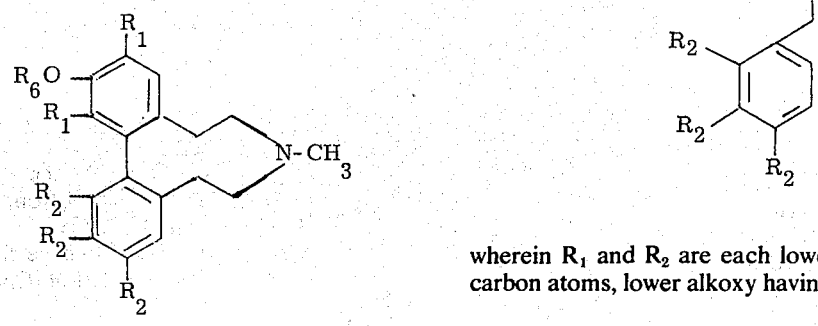

wherein $R_1$ and $R_2$ are each lower alkyl having 1 – 7 carbon atoms, lower alkoxy having 1 – 7 carbon atoms, or hydrogen, $R_6$ is a lower alkyl group having 1 – 7 carbon atoms, $R_5$ is a lower acyl group of the form RCO wherein R is a lower alkyl group having 1 – 7 carbon atoms, or is hydrogen, or $R_5$ is a lower alkyl group having 1 – 7 carbon atoms, with an oxidizing agent, as above defined; and with a solvent as above defined to form a combination of (±) N-formylnoraporphines and (±) spirodienones. The (±) spirodienones may be separated, if desired, and treated with a Lewis acid in the presence of a dry alkanol. Suitable Lewis acids include HCl, paratoluene sulfonic acid, zinc chloride or the like. Suitable alkanols are the lower 1 – 7 carbon atom alkanols, such as methanol, ethanol or the like. The resulting ketal is then treated with an excess of $LiAlH_4$ in THF to yield the dibenzazonine derivative.

Having now generally described this invention, a further understanding can be attained by reference to certain specific examples which are provided herein for purposes of illustration only and are not intended to be construed as limiting of the invention unless otherwise so indicated.

EXAMPLE 1

Papaverine, a readily available alkaloid, of the formula

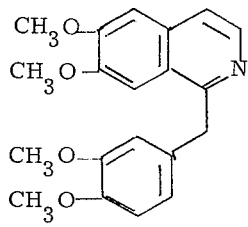

was used as the reactant. $VOF_3$ in an amount of 2.7 g (22 mmol) was added to a solution of papaverine (0.975 g. 3 mmol) in trifluoroacetic acid (30 ml) at 0°C under a nitrogen atmosphere to protect against possible interference from atmospheric moisture. The mixture was stirred for about 3 hours and then was poured into 60 ml of cold water containing 10 g of citric acid. The acid was introduced to reduce excess oxidant and to complex with any metal ions present during the subsequent basification. The mixture was made basic with 5% $NH_4OH$ and extracted with $CHCl_3$ until the extract was colorless. The yield after concentration and filtration of the $CHCl_3$ extract through a column of alumina was 80%. An aryl-aryl intermolecularly coupled product of the formula:

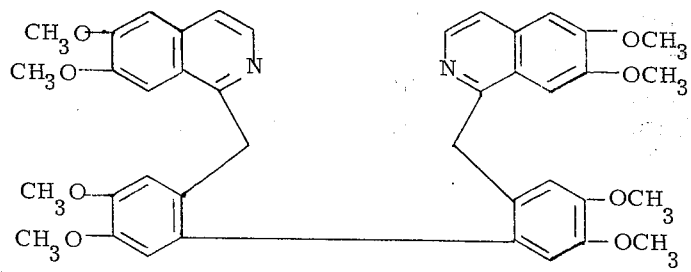

was confirmed by analytical and spectral data: mp 180°–182°; uv $\lambda_{max}^{EtOH}$ (log ε) 239 (5.06, 284 (4.14), 3.14 (3.85), 328 (3.91) nm; nmr ($CDCl_3$) δ8.23 (d, J=6 Hz, 2H-3), 7.23 (d,J=6 Hz, 2H=4), 6.93 (s, 4ArH), 6.72 (s,2ArH, 6.50 (s, 2ArH), 4.23 (s,4H, 2Ar-$CH_3$); mass spectrum m/e (%) 676 (19, $M^+$), 475 (100). Assignment of the 6'–6' linkage in the structure of the dimer, favored by analogy to the products of other reactions of papaverine was confirmed by oxidation to the tetramethoxydiphenic. Reduction of the dimer with Zn-40% aqueous HOAc at 90° to the bis-tetrahydro derivative was followed by $CH_3I$-methylation and Hofmann degradation to the bis-methine. Oxidation with aqueous $KMnO_4$ yielded a crude dialdehyde, which was oxidized with $KMnO_4$/acetone to the diacid of the formula:

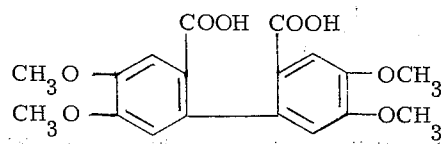

mp 251°–254° (lit[11] mp 251°–253°); mass spectrum m/e (%) 362 (80, $m^+$), 344 (48), 317 (100).

The dipapaverine possesses significant tumor inhibitory activity against the Walker 256 intramuscular carcinosarcoma in rats.

EXAMPLE 2

The reaction of Example 1 was repeated except with the use of (±)-laudanosine which has the formula

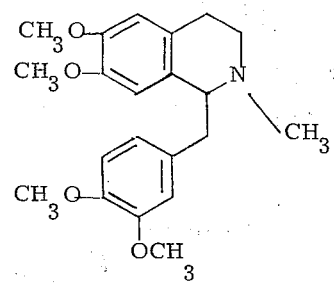

Intramolecular coupling proceeded readily upon treatment of a solution of the laudanosine in $FSO_3H$, $CH_2Cl_2$, and TFA at −30° with a solution of $VOF_3$ in TFA. The product, (±)-glaucine of the formula

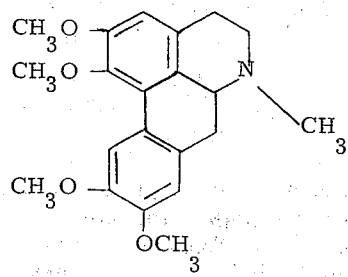

was isolated as the hydrobromide: mp 220°–221° (42%, identical with a sample prepared from authentic (±)-glaucine); free base: mp 137°–139°.

Glaucine has been reported to have antitussive properties, by V.V. Berezhivskaya et al, Chem. Abstr. 68, 94521 g (1968).

EXAMPLE 3

The reaction of Example 1 was again repeated except with the use of (±)-N-formylnorlaudanosine of the formula

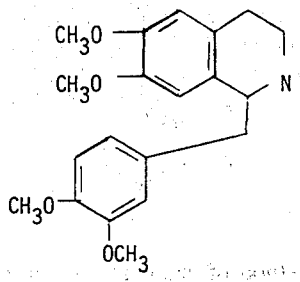

The reaction was conducted in $CH_2Cl_2$ and TFA was treated at −30° with $VOF_3$ in TFA. The products were (±)-N-formylnorglaucine

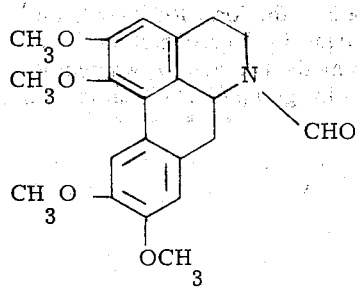

(6%, mp 209°–212°) and (±)-spirodienone

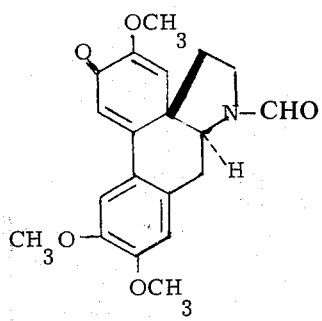

(55%): mp 243°–245°; uv $\lambda_{max}^{EtOH}$ (log ε) 236 (sh, 4.08), 265 (4.07), 291 (3.79), 359 (3.99) nm; ir $\lambda_{max}^{KBr}$ 6.02, 6.14μ; nmr[14] (TFA)δ8.32 and 8.14 (s, 1H, CHO), 7.28, 7.22, 7.07, 6.88, 6.84, and 6.82 (all s, 3H, ArH), 6.34 (s, 1H, ArH), 3.99, 3.92, and 3.88 (s, 9H, 3-OCH₃); mass spectrum m/e (%) 355 (100, M⁺), 327 (50), 297 (100). The structure of

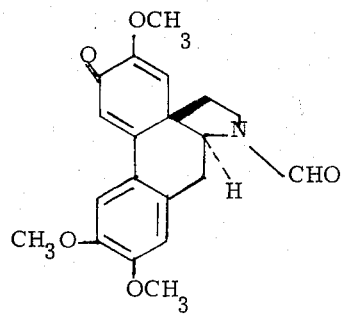

spirodienone was established by x-ray analysis using symbolic addition methods. The crystals were found to be monoclinic, $a$=8.02(2), $b$=18.56(3), $c$=12.30(2) A, and $\beta$=109°30′. The space group is $P2_1/c$ with Z=4. All hydrogen atoms except those associated with the C-9 methoxy group have been located and R is 0.04 for 1450 reflections after least-squares refinement with anisotropic thermal parameters assumed for the non-hydrogen atoms.

Treatment of the spirodienone in methanol with dry HCl gas gave the ketal

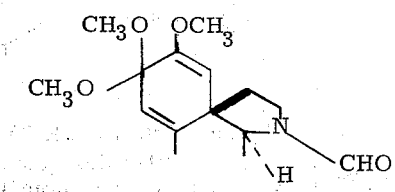

(71%): mp 107°–109°; ir $\lambda_{max}^{KBr}$ 5.99μ; mass spectrum m/e 401 (M⁺). Room temperature treatment of the ketal in THF with an excess of $LiAlH_4$ gave O-methylerybidine,

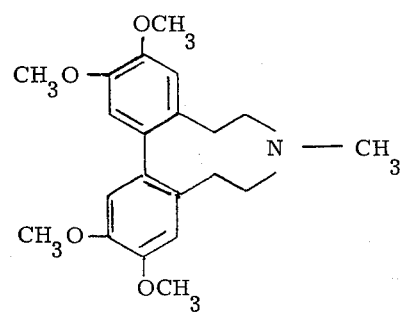

O-methylerybidine (a dibenzazonine)

81%, mp 139°–140°, mixture mp, mixture tlc, and mass spectrum identical to those of a sample prepared by diazomethane methylation of erybidine.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method for effecting oxidative intramolecular coupling of a compound of the formula

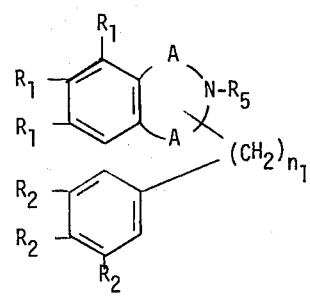

wherein $n_1$ is an integer of from 1 – 3; each $R_1$ and $R_2$ may be a lower alkyl having 1 – 3 carbon atoms, lower alkoxy havng 1 – 7 carbon atoms or hydrogen, with the proviso that at least one of each $R_1$ and $R_2$ are lower alkoxy, and wherein the ring system defined by -A-N-A- and the two carbon atoms shared in common with the adjacent benzene ring is selected from the group consistng of

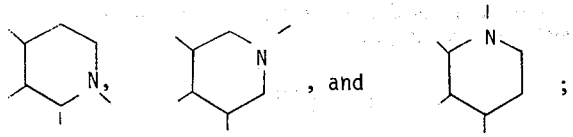, and $R_5$ is lower alkyl acyl group of the form RCO wherein R is a lower alkyl having 1–7 carbon atoms, or is hydrogen, or $R_5$ is hydrogen or a lower alkyl group having 1 – 7 carbon atoms, with an oxidant selected from the group consisting of $VOF_3$, $MoOCl_4$, $Pb_3O_4$, $Tl(CF_3COO)_3$, $CrO_3$, $MnO_2$, $Co(OH)_3$, $Ce(NH_4)_2(NO_3)_6$ and $Ce(SO_4)_2$ at $-45°$ to $60°C$ to form a cyclized compound of the formula:

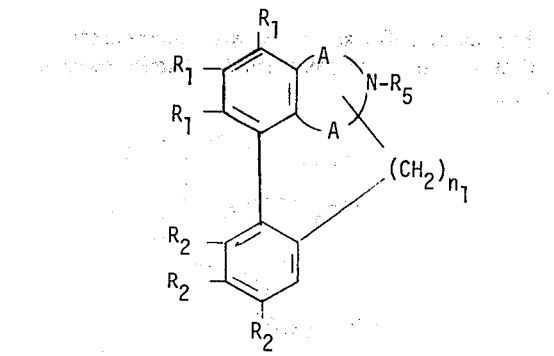

2. The method of claim 1, wherein said reactant is ±-laudanosine.

3. The method of claim 1, wherein said reactant is ±-N-formylnorlaudanosine.

4. The method of claim 1 wherein $R_5$ is a loweralkyl acyl group of the form RCO containing a lower alkyl group having 1 – 7 carbon atoms.

5. The method of claim 1, wherein $R_5$ is hydrogen or a lower alkyl group of 1 – 7 carbon atoms.

* * * * *